(12) United States Patent
Levatter et al.

(10) Patent No.: US 12,005,266 B2
(45) Date of Patent: *Jun. 11, 2024

(54) DEVICE FOR TARGETED TREATMENT OF DERMATOSIS

(71) Applicant: STRATA SKIN SCIENCES, INC., Horsham, PA (US)

(72) Inventors: Jeffrey I. Levatter, Rancho Santa Fe, CA (US); David Brooks, Oceanside, CA (US)

(73) Assignee: STRATA SKIN SCIENCES, INC., Horsham, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/858,524

(22) Filed: Dec. 29, 2017

(65) Prior Publication Data

US 2018/0140867 A1    May 24, 2018

Related U.S. Application Data

(63) Continuation-in-part of application No. 15/323,936, filed as application No. PCT/US2014/058957 on Oct.
(Continued)

(51) Int. Cl.
*A61N 5/06*    (2006.01)
*A61N 5/067*    (2006.01)

(52) U.S. Cl.
CPC .......... *A61N 5/0616* (2013.01); *A61N 5/062* (2013.01); *A61N 2005/0627* (2013.01);
(Continued)

(58) Field of Classification Search
CPC .......... G02B 5/208; G02B 5/201; G02B 5/22; G02B 5/226; G02B 5/223;
(Continued)

(56) References Cited

U.S. PATENT DOCUMENTS

2003/0228476 A1* 12/2003 Buhay ............... B32B 17/10036
428/469
2004/0158300 A1* 8/2004 Gardiner ............. A61N 5/0619
607/88
(Continued)

FOREIGN PATENT DOCUMENTS

CN    2719223 Y  *  8/2005
CN    2719223 Y     8/2005
(Continued)

OTHER PUBLICATIONS

Supplementary European Search Report for co-pending European Patent Application No. 15827333 mailed Feb. 6, 2018.

*Primary Examiner* — Shirley X Jian
*Assistant Examiner* — Vynn V Huh
(74) *Attorney, Agent, or Firm* — Gottlieb, Rackman & Reisman, P.C

(57) ABSTRACT

A device for applying targeted phototherapy to an area of diseased skin to place a skin condition into remission and a method of determining a maximum tolerable dose of phototherapy applied to a treatment area of diseased skin to determine an optimum therapeutic dose to quickly place a skin condition into remission. The device can include a housing and an optical matrix arranged within the housing that are attached to a dosimetry device. The optical matrix includes a plurality of at least one of absorptive, reflective and/or partially transmissive regions or arrays of perforations that each permits a different percentage of light to be delivered to an individual's skin. Jigs can be included to arrange a plurality of varying exposures to be placed on the patient's skin. An assessment can then be made as to the maximum tolerable dose of phototherapy that can be applied to the individual's skin in order to place a skin condition into remission.

21 Claims, 12 Drawing Sheets

Related U.S. Application Data 3, 2014, now abandoned, application No. 15/858,524 is a continuation-in-part of application No. 14/815,424, filed on Jul. 31, 2015, now Pat. No. 11,471,695, which is a continuation of application No. PCT/US2015/042926, filed on Jul. 30, 2015.

(60) Provisional application No. 62/137,086, filed on Mar. 23, 2015, provisional application No. 62/031,674, filed on Jul. 31, 2014, provisional application No. 61/886,805, filed on Oct. 4, 2013.

(52) U.S. Cl.
CPC ............... *A61N 2005/0628* (2013.01); *A61N 2005/0644* (2013.01); *A61N 2005/0661* (2013.01); *A61N 5/067* (2021.08)

(58) Field of Classification Search
CPC .......... G02B 2005/1804; G02B 5/1838; G02B 5/0278; G02B 5/283; G02B 5/28; G02B 5/3075; G02B 5/3091; G02B 1/00; G02B 1/04; G02B 1/10; G02B 1/08; G02F 1/00; G02F 1/0018; G02F 1/0063; G02F 1/01; A61N 5/0616; A61N 2005/0658; A61N 2005/0627; A61N 2005/0628; A61N 2005/0644; A61N 2005/0661; A61N 2005/067; A61N 5/06–2005/073; A61B 18/20–18/28

USPC ..................................... 607/88–94; 606/2–19
See application file for complete search history.

(56) References Cited

U.S. PATENT DOCUMENTS

| | | | |
|---|---|---|---|
| 2005/0063045 A1* | 3/2005 | Sakakibara | G01J 1/08 359/361 |
| 2006/0195166 A1* | 8/2006 | Minamoto | A61B 5/445 607/94 |
| 2006/0247609 A1 | 11/2006 | Mirkov et al. | |
| 2007/0016074 A1 | 1/2007 | Abreu | |
| 2009/0160341 A1 | 6/2009 | Justel et al. | |
| 2012/0109042 A1 | 5/2012 | Koo et al. | |
| 2013/0018442 A1 | 1/2013 | Irwin et al. | |

FOREIGN PATENT DOCUMENTS

| | | | |
|---|---|---|---|
| CN | 201230877 Y | * | 5/2009 |
| CN | 201230877 Y | | 5/2009 |
| CN | 202151357 U | * | 2/2012 |
| CN | 202151357 U | | 2/2012 |
| WO | 2005007003 | | 1/2005 |
| WO | 2016019151 | | 2/2016 |

* cited by examiner

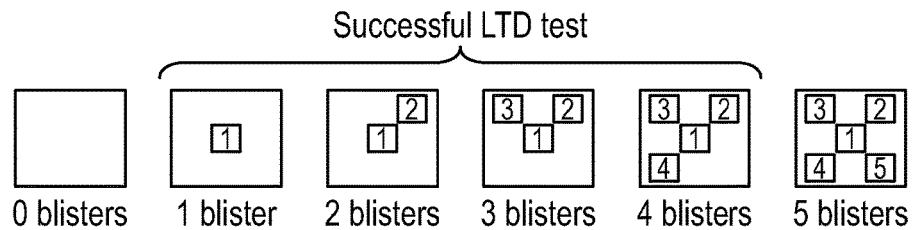
FIG. 9
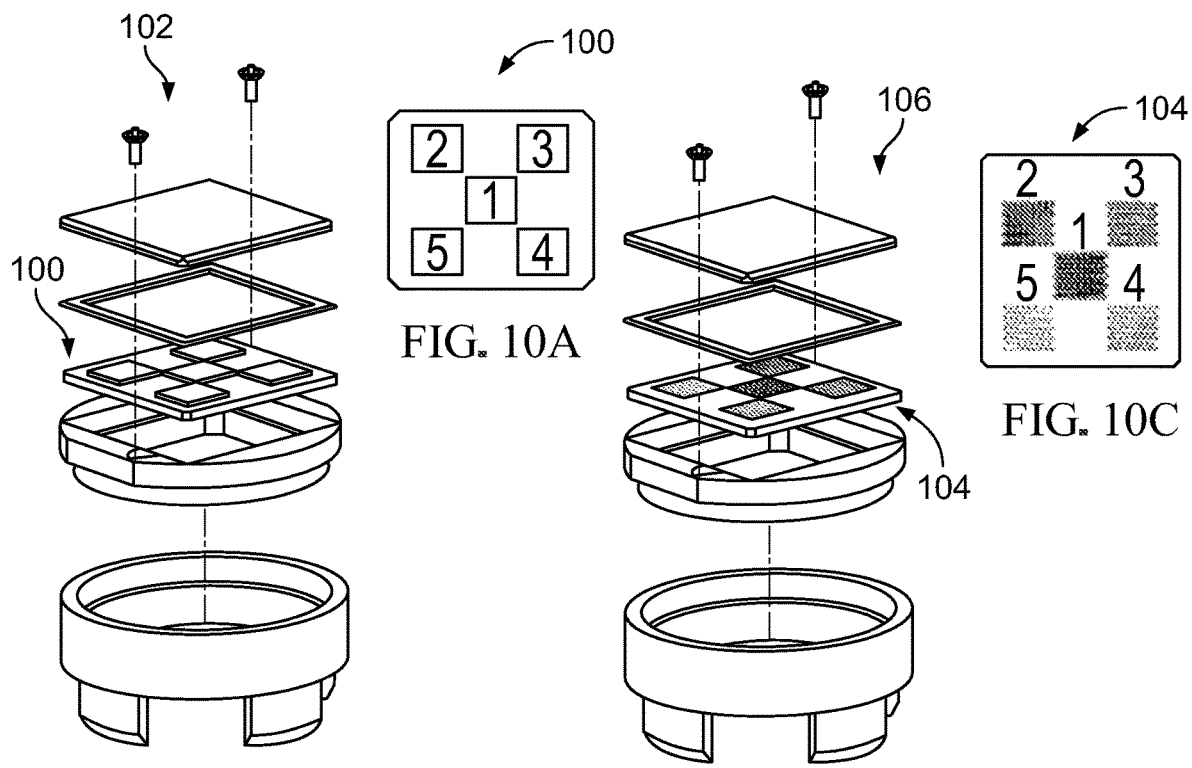
FIG. 10E
FIG. 10A
FIG. 10B
FIG. 10C
FIG. 10D

DEVICE FOR TARGETED TREATMENT OF DERMATOSIS

CROSS-REFERENCE TO RELATED APPLICATIONS

This patent application is a continuation in part of U.S. patent application Ser. No. 15/323,936, which is a National Stage Entry of PCT/US2014/058957 filed Oct. 3, 2014, which claims benefit under 35 U.S.C. § 119 to U.S. Provisional Patent Application No. 61/886,805 filed Oct. 4, 2013 and continuation in part of U.S. patent application Ser. No. 14/815,424, filed Jul. 31, 2015, which is a continuation of PCT/US2015/042926, filed Jul. 30, 2015, which claims benefit under 35 U.S.C. § 119 to U.S. Provisional Patent Application No. 62/031,674, filed Jul. 31, 2014, and U.S. Provisional Patent Application No. 62/137,086, filed Mar. 23, 2015, which are hereby incorporated in their entirety by reference as part of the present disclosure.

FIELD OF THE INVENTION

The present invention relates generally to targeted phototherapeutic treatment of skin conditions and more particularly to dispensing a dosage of light and dispersing it into a plurality of dosages of varying intensity levels (energy/unit area) of light onto an individual's skin to determine an optimum therapeutic dosage of phototherapy that can be administered to the individual to aid in the treatment of a skin condition.

BACKGROUND OF THE INVENTION

Methods and apparatuses for targeted phototherapy (e.g., narrow-band, 308 nm excimer lasers dispensing ultraviolet light energy) are known as an effective and safe treatment for various dermatoses (e.g., psoriasis, vitiligo, leukoderma, atopic dermatitis, and alopecia areata).

Psoriasis, vitiligo and other skin conditions affect millions of people. These dermatoses can range from mild to severe and can lead to substantial morbidity, psychological stress and can have a profound negative impact on the quality of life of an individual suffering from a skin condition. Although available therapies can reduce the extent and severity of these diseases and improve an individual's quality of life, reports have indicated dissatisfaction with the effectiveness, cost, and inconvenience of current treatment modalities.

There are various types of psoriasis a person can be diagnosed with depending on the affected area of the person's body and/or their symptoms. Plaque psoriasis (e.g., psoriasis vulgaris), which accounts for about 80% to about 90% of patients, typically appears as red blotches or patches with dry, silvery scales. Guttate psoriasis appears as numerous small round spots. Flexural psoriasis (inverse psoriasis) can typically be found in skin folds and appears as smooth inflamed patches of skin. Pustular psoriasis appears as raised bumps. Erythrodermic psoriasis usually causes with severe itching, swelling, and pain that may involve the widespread inflammation and exfoliation of the skin. Fingernails and toenails may be affected by nail psoriasis, and often undergo a variety of changes in the appearance that can include small indentations in the nails (e.g., pitting), lifting, discoloration, thickening, and crumbling.

A common treatment modality for individuals with psoriasis or vitiligo is to receive phototherapy administered at phototherapy centers. At these centers, individuals are exposed to narrowband (NB) or broadband (BB), UVB light (290-320 nm), or a therapy of psoralen plus ultraviolet light (320-400 nm) within an A range (PUVA). Ultraviolet light reduces the symptoms of psoriasis through immunomodulatory mechanisms. The treatment of atopic dermatitis and alopecia areata with UV light has also been studied, but not to the same degree. Treatment for leukoderma and vitiligo rely on UV light to help re-pigment the skin due to a lack of melanin/melanocytes.

The severity of psoriasis can be classified or "scored" in a variety of ways. In a classification method that is based on the surface area of tissue affected, psoriasis can be graded as mild (e.g., affecting less than about 3% of the total area of the body surface (BSA)), moderate (e.g., affecting about 3% to about 10% BSA), or severe (e.g., affecting more than about 10% BSA). To put the percentages into perspective, the palm of a person's hand is about 1% BSA. Other scales may also be employed for measuring the severity of psoriasis. For example, in addition to the size of affected or influenced BSA, factors such as the condition duration, the frequency of disease recurrence, disease activity (e.g., degree of plaque redness, thickness, and scaling), response to previous therapies, and the impact of the disease on the person may also be considered to determine the severity of the disease.

A subject having less than 3% BSA affected by the condition may be considered to have moderate or severe psoriasis if the affected area is accompanied by radical symptoms such as swelling or pain. A subject having a psoriasis condition that is resistant or recalcitrant to one or more known treatments may also be considered to have severe psoriasis regardless of the size of influenced area. Therefore, psoriasis may be characterized as severe if at least one of the following is observed: the area of influenced tissue is greater than about 10% BSA; the condition (e.g., accompanied by pain and/or swelling) persists for a month or more; the disease activity is substantially active; and the disease is resistant to one or more of known treatments. Psoriasis may also be considered severe if the diseased area comprises between about 10% and about 20% BSA of the subject, between about 20% and/or about 30% BSA, or greater than about 30% BSA.

Severity of psoriasis may also be determined according to standard clinical definitions. For example, the Psoriasis Area and Severity Index (PASI) assess psoriasis disease intensity based on the quantitative assessment of three typical signs of psoriatic lesions: erythema, infiltration, and desquamation, combined with the skin surface area involvement in the head, trunk, upper extremities, and lower extremities. PASI scores range from 0 (no disease) to 72 (maximum disease), in which higher scores indicate greater disease severity. Improvements in psoriasis are indicated, for example, as "PASI 50" (50% improvement in PASI from baseline) (e.g., "PASI 90" is a 90% improvement in PASI from baseline). The Physicians Global Assessment (PGA) also assesses psoriasis activity and clinical response to treatment. PGA is a six-point score that summarizes the overall quality (erythema, scaling, and thickness) and extent of plaques relative to the baseline assessment. A patient's response is rated as worse (negative clearance (disease became worse), poor (0-24% clearance), fair (25-49% clearance), good (50-74% clearance), excellent (75-99% clearance), or cleared (100% clearance). Other measures of improvement in the disease state of a psoriasis patient may include clinical responses such as the Dermatology Life Quality Index (DLQI), the Short Form 36 Health Survey (SF-36), and the European Quality of Life-5 Dimensions (EQ-5D).

With conventional UVB phototherapy, dosing is predicated on either an individual's Fitzpatrick Skin Type (i.e., skin color and darkness) in conjunction with the thickness of the psoriatic plaque or on a measurement of an individual's minimum erythemal dose (MED) An individual's minimum erythemal dose is the dose of UVB that generates a significant red erythemal skin response in normal/healthy tissue. Dosing higher than an individual's minimum erythemal dose tolerance level can result in undesirable (i.e., more severe) tissue reactions, and even blistering. However, neither of these two methods of determining an individual's appropriate dosing protocol is therapeutically optimal and typically results in dosing at levels that are far too conservative which in turn results in a reduced therapeutic benefit. This is because using the Fitzpatrick Skin Type is merely a guess at an individual's maximum tolerable dose (MTD) (based on historical norms that do not apply to many individuals) and the fundamental limitations of the minimum erythemal dose method that only measures the tolerance of the healthy/normal tissue, not the diseased tissue being treated. In either case, many individuals are regularly administered sub-optimal UVB dosing when clinicians, recognizing that current dosing paradigms are only a crude guess, initiate dosing at even lower levels than might be expected. They do so to avoid unintentional dosing at higher levels than the minimum erythemal dose that might be above an individual's minimal blistering dose (MBD) leading to extreme erythema, blistering, and possible injury. This problem is enhanced by the fact that the optimum dose (i.e., MTD, a dose that is near, but just lower than the MBD) can vary greatly for each individual, making it very difficult, if not impossible, to correctly gauge an individual's optimal dose. As such, the lack of having an objective means of determining an individual's minimal blistering dose prevents clinicians from dosing more effectively at an individual's optimum dose level, which could significantly lower the total number of required UVB treatment sessions to obtain the desired clinical outcome.

As a result of the typically high number of treatment sessions required, the use of phototherapy is commonly limited due to the overall inconvenience of the therapy. Poor compliance with the necessary regimen of regular treatment sessions is common because of the time, travel and the cost, in many cases, to effectively treat the disease. Other less effective therapies (e.g., topical prescriptions and over-the-counter topical creams) are often an individual's more convenient fallback option.

SUMMARY OF THE INVENTION

The present invention is directed to a dosimetry device that aids in determining an individual's optimum dose of phototherapy to aid in the treatment of a skin condition by quickly and easily measuring the individual's phototherapeutic tolerance by assessing the individual's minimum blistering dose on diseased skin in order to then treat a skin condition at or near the individual's maximum tolerable dose.

In an embodiment, the present invention is directed to a method for treating a skin disease comprises the steps of administering a plurality of doses of phototherapy at increasing intervals to area of diseased skin (e.g., psoriasis), analyzing the area of the diseased skin and assessing the doses at which burning and blistering of the diseased skin occurs, determining a maximum interval of phototherapy that can be administered to the diseased skin and treating the diseased skin below or at the maximum dose. The skin disease can be treated at approximately about at least one of a minimal blistering dose, at one or two levels below a minimal blistering dose or at about a minimal erythema dose. By treating a skin condition at or near an individual's maximum tolerable dose on diseased skin, the overall number of treatment sessions required to place an individual's skin condition into remission can be greatly reduced.

In an embodiment, the present invention is directed to a dosimetry device that is connectable to a phototherapy apparatus for applying targeted phototherapy to a treatment area (e.g., on diseased skin tissue). The device comprises a housing and an optical matrix arranged within the housing that includes a plurality of at least one of absorptive, reflective and/or partially transmissive regions, which each permit a different intensity of light (expressed as percentages of an incident of a light beam) and/or range of light to pass therethrough. In an embodiment, the light that is dispensed from a phototherapy apparatus is UVB light.

The optical matrix can be connected to the housing or can be formed within the housing. In an embodiment, the optical matrix can include at most nine regions. In an embodiment, the optical matrix can include five regions. In an embodiment, the intensity of light passing through the regions can range from about 20% in one region up to about 100% in another region. In another embodiment, the intensity of light passing through the regions ranges from about 0% in one region up to about 90% in another region.

The optical matrix can be substantially square and can be about 2 cm by 2 cm with each region sized to be approximately about 5 mm by 5 mm. Each of the regions of the optical matrix can be square, rectangular, circular, or ovoid. Each of the regions can include at least one of a metallic, multi-dielectric and a dielectric coating or volume absorbing materials in a UVB range. The reflective coatings can be configured for an output UVB light of about 308 nm. Each of the regions of the optical matrix can include at least one of metallic or a dielectric coating. Each of the regions of the optical matrix can include a different filter.

The plurality of transmissive regions can comprise a metal membrane comprising a symmetric array of perforations of different density. The metal membrane can comprise a stainless steel membrane, fused silica or UV transmitting plastic. The transmitting plastic can be acrylic or cyclic olefin copolymer. The transmitting plastic can be coated with multi-layer dielectric materials or coated with enhanced aluminum. The transmission of light passing through the regions can range from about 20% in one region up to about 100% in another region. In another embodiment, the transmission of light passing through the regions can range from about 0% in one region up to about 90% in another region.

In an embodiment, the present invention is directed to a method of determining a maximum tolerable dose of phototherapy that is capable of being applied to diseased skin tissue to aid in the treatment of a skin condition. The method comprises the steps of providing a dosimetry apparatus that comprises a housing and an optical matrix comprising a housing and a jig arranged within the housing that includes a plurality of at least one of absorptive, reflective and/or partially transmitting regions to permit varying transmissions of light to pass therethrough, connecting the dosimetry apparatus to a phototherapy apparatus that is configured to disperse UVB light, arranging the phototherapy apparatus at or near the treatment area and transmitting the UVB light from the phototherapy apparatus and through the regions of the optical matrix such that varying doses of the UVB light will be applied simultaneously or sequentially to the various areas under treatment. The UVB light can be transmitted at approximately about 308 nm In an embodiment, percentages of the UVB light passing through positions of the jig can range from about 20% in one region up to about 100% in another region. In another embodiment, the percentages of the UVB light passing through the positions of the jug ranges from about 0% in one region up to about 90% in another region.

In an embodiment, the method can further comprise the step of analyzing the treatment area subsequent to transmitting the varying percentages of the UVB light to the treatment area through the optical matrix to assess the minimum blistering dose of the treatment area.

In an embodiment, the method can further comprise the step of analyzing the treatment area subsequent to applying the UVB light to the treatment area, for example, approximately 24 to 48 hours after the UVB light is applied thereto, to assess the minimum blistering dose of the skin being treated. In an embodiment, the method can further comprise the step of applying a maximum tolerable dose of the UVB light to the treatment area based on the minimum blistering dose pf the UVB light from an analysis of the varying percentages of the UVB light to the treatment area through the optical matrix or jig to determine a near optimum therapeutic dose without blistering the treated area.

BRIEF DESCRIPTION OF THE DRAWINGS

FIG. 9 is a diagram depicting results of an exposure of a patient's skin to different levels of UV light through the end piece depicted in FIG. 5;

FIG. 10A is a top view of an embodiment of a filter fabricated with a desired number of windows through which UV light can be transmitted;

FIG. 10B is an assembly view of an embodiment of a tip of an excimer phototherapy system with the filter of FIG. 10A included as part of the assembly;

FIG. 10C is a top view of an embodiment of a filter that includes a plurality of patterns etched thereon;

FIG. 10D is an assembly view of an embodiment of a tip of an excimer phototherapy system that includes the filter of FIG. 10C;

FIG. 10E is a chart comparing the filter of FIG. 10A with the filter of FIG. 10C;

DETAILED DESCRIPTION OF EMBODIMENTS OF THE INVENTION

As discussed above, known phototherapy treatment of skin disorders (e.g., psoriasis) involves testing non-affected areas of a patient's skin tissue by applying doses of varying levels of UV light in an attempt to determine the patient's maximum tolerable dose. However, diseased skin, has a much higher tolerance to UV light than non-affected skin. Thus, testing non-affected areas of skin does not provide an accurate assessment of the patient's tolerance and in turn maximum dosage that can be applied to a region of the patient's skin that is affected by a skin disorder. In an embodiment, diseased skin is treated by UV light applied directly thereto.

Figure 1A:
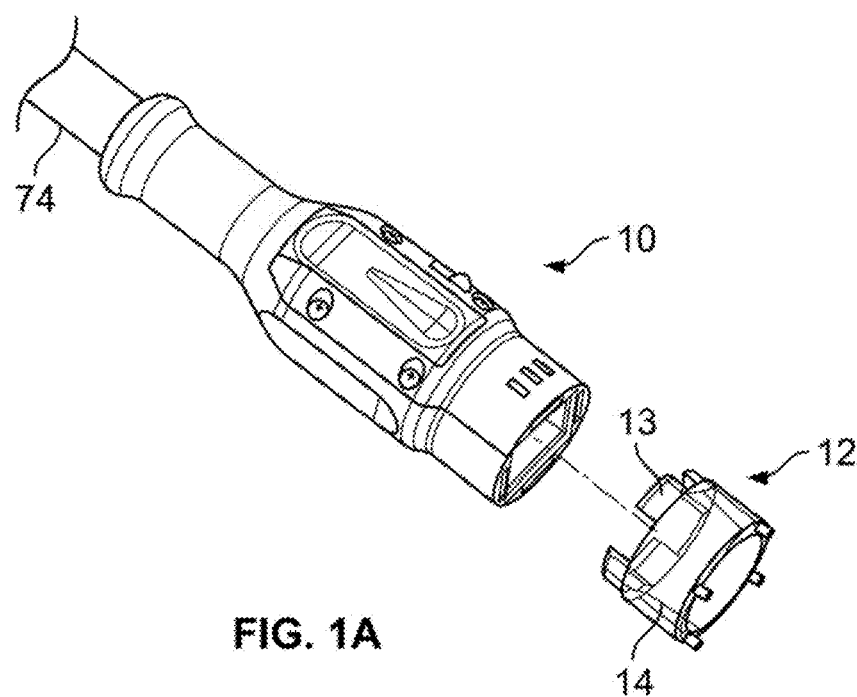
FIG. 1A is a perspective view a hand-held phototherapy delivery apparatus and an end piece that is connectable to the delivery apparatus.
Figure 1B:
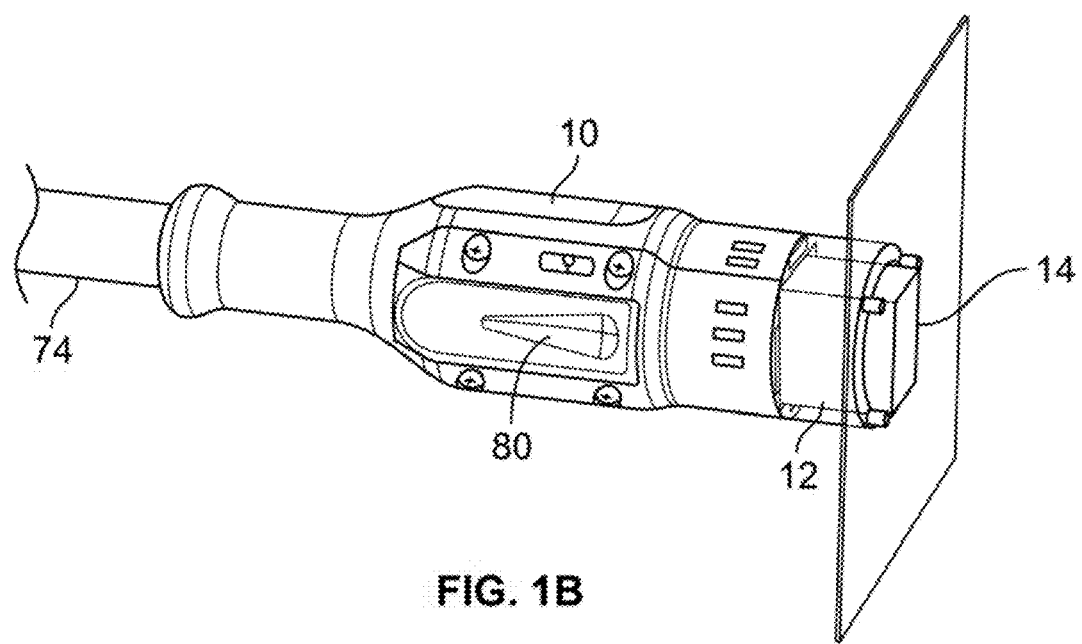
FIG. 1B is a perspective view the hand-held phototherapy delivery apparatus and end piece of FIG. 1A with the end piece attached to the delivery apparatus and a beam of light extending through the end piece.
Figure 1C:
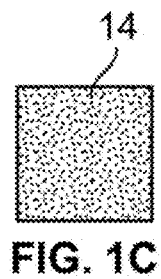
FIG. 1C is an end view of the beam of light extending through the end piece of FIG. 1B.

With reference now to the drawings, FIGS. 1A through FIG. 1C illustrate an embodiment of a delivery apparatus 10 and an tip 12 that is connectable thereto to deliver a beam of light 14 that is dispensable from the delivery apparatus 12 into a desired shape so as to apply targeted phototherapy as a treatment modality onto the skin of an individual suffering from a skin condition. As shown in FIG. 1A, the tip piece 12 includes a plurality of tabs 13 that extend from one end of the tip piece 12 in a first direction and that are configured to releasably connect the tip piece 12 to the laser delivery apparatus 10.

As shown in FIGS. 1B and 1C, in an embodiment, the tip piece 12 can size and dispense a square beam 14 of light from the delivery apparatus 10 that can be, for example, 2 cm by 2 cm. An end view of such a square beam 14 of light is illustrated in FIG. 3C.

Figure 2:
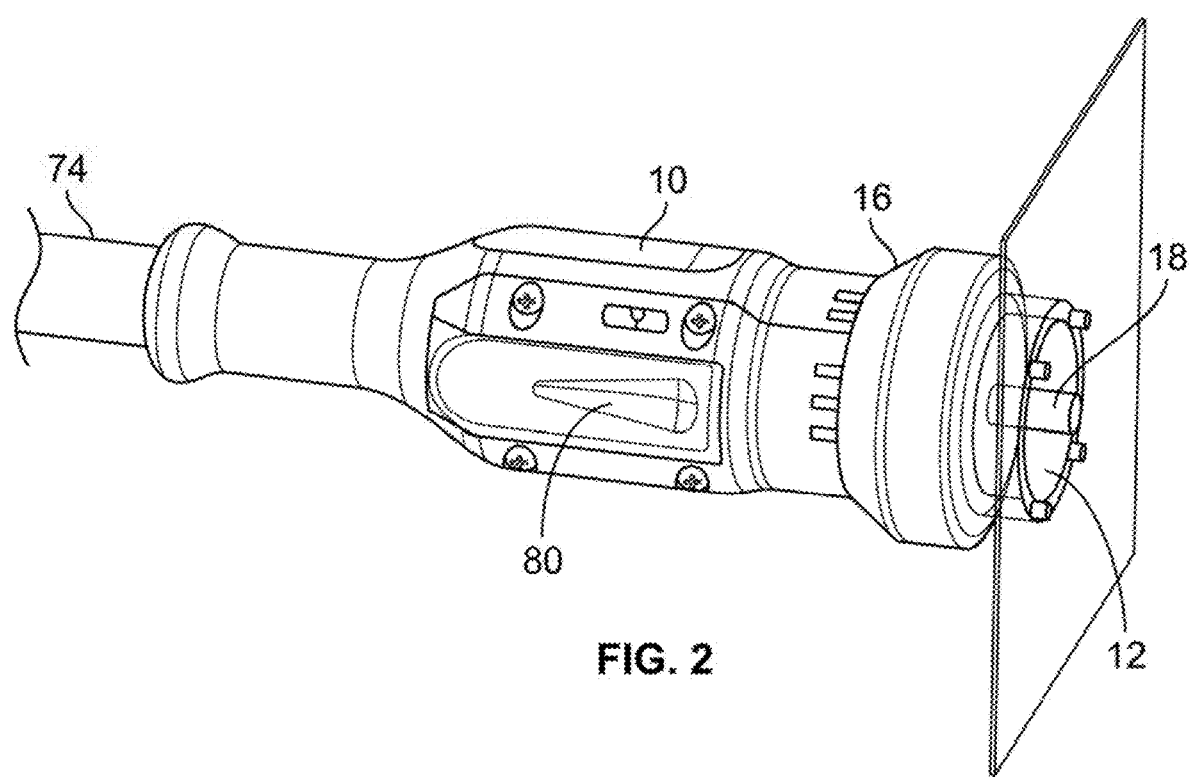
FIG. 2 is a perspective view the hand-held phototherapy delivery apparatus and an embodiment of an end piece with a circular diaphragm connected thereto for beam shaping.

As depicted in an embodiment in FIG. 2, the hand-held phototherapy delivery apparatus 10 and the tip piece 12 can include a diaphragm 16 that partially encompasses the delivery apparatus 10 and the end piece 12 to aid in shaping a beam of light 18. Here, the beam of light 18 is cylindrical.

Figure 3A:
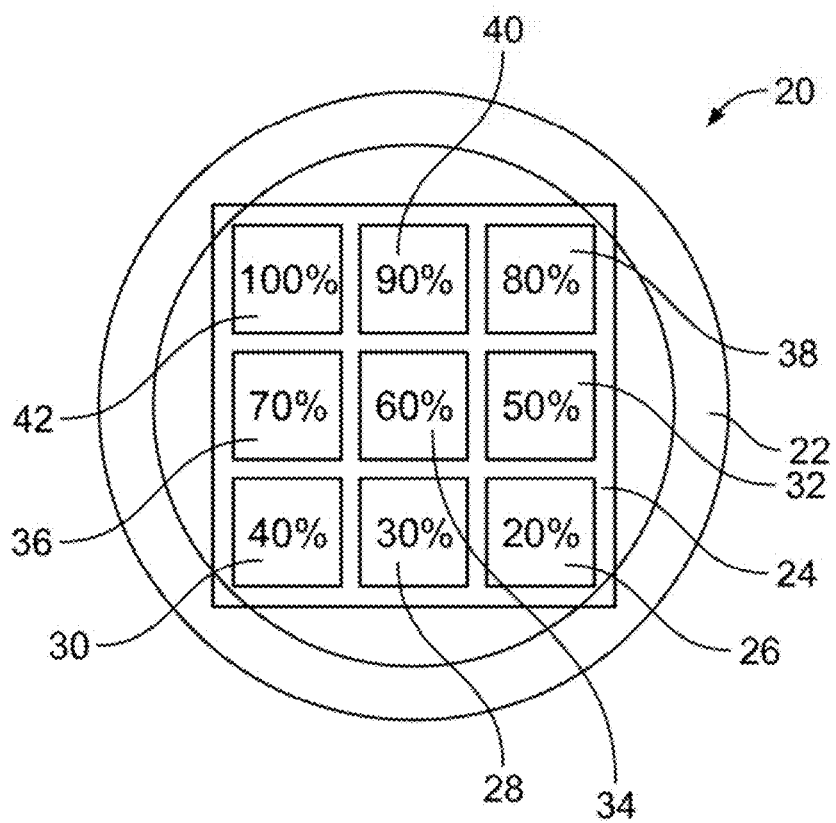
FIG. 3A is a front view of an embodiment of the dosimetry device of the present invention illustrating an embodiment of the photosensitivity matrix.

FIG. 3A illustrates a dosimetry device 20 that can distribute a dose of light energy into a plurality of doses of varying levels of light energy that can then be applied onto a treatment area simultaneously or sequentially, to determine an optimum therapeutic dose of phototherapy for an individual suffering from a skin condition by measuring the individual's minimum blistering dose of phototherapy. By treating an individual suffering from a skin condition at or near their minimum blistering dose, the overall number of treatment sessions required to place the individual's diseased skin into remission can be greatly reduced while burning of the individual's skin can be substantially reduced and in most instances avoided. In turn, an individual will be much more likely to be seeking out necessary continued treatment of a skin condition due to time and cost savings from known treatment procedures and the lower risk of significant discomfort from blistering than known treatment procedures.

As shown in an embodiment in FIG. 3A, the dosimetry device 20 includes a housing 22 that is configured to be releasably connected the phototherapy delivery apparatus 10 with a sensitivity matrix 24 arranged within the housing 22. As shown in embodiments in FIG. 3A through FIG. 5, the housing 22 of the device 20 is cylindrical. However, the shape of the housing 22 can be any shape, including, but not limited to, square, rectangular, elliptical, triangular, and trapezoidal. The sensitivity matrix 24 can be connected to the housing 22 in any known manner.

UV phototherapy utilizes light in the UVB band, which extends in wavelength between about 280 nanometers and about 320 nanometers. Psoriasis-afflicted tissue can be effectively rehabilitated with light having wavelengths between about 300 nanometers and about 310 nanometers. Light having a wavelength spectrum between about 295 nanometers and about 325 nanometers can be effective in healing the tissue as well. However, due to the intensity of the light applied to a patient, there is a risk of some undesirable side effects of phototherapy to treat psoriasis and other skin conditions such as DNA damage (e.g., skin cancer). Therefore, to treat diseased skin and joints of a subject under conditions that can maximize a likelihood of placing the diseased tissue into remission while minimizing the risk of erythema and/or DNA damage, a physician will typically treat a patient in a range of between about 295 nanometers and about 320 nanometers, more specifically, between about 300 nanometers and about 310 nanometers, and even more specifically at about 308 nanometers.

The fluence of light having wavelengths distributed between about 300 and about 310 nanometers has been determined to range between about 500 mJ/cm2 and about 5000 mJ/cm2. More specifically, the fluences preferably range between about 100 mJ/cm2 and about 8 J/cm2, and between about 300 mJ/cm2 and about 3 J/cm2. Other dosages are also possible depending upon where blistering of the plaque takes place. To determine such blistering the laser radiation may be applied in increments of typically 50, 100 or 200 mJ/cm2.

In an embodiment, one or two such treatments can provide significant improvement of the afflicted area of skin as opposed to 20 treatments by prior methodology.

In embodiments, phototherapy comprises an average power of between about 0.3 watts and about 0.5 watts, between about 2 watts and about 3 watts, between about 2.5 watts and about 4.5 watts, or between about 4.8 watts and about 7.2 watts. Other average powers are also possible (e.g., 10 watts or more). In embodiments, phototherapy comprises energy between about 8 mJ/pulse and about 15 ml/pulse or between about 12 mJ/pulse and about 18 mJ/pulse. Other pulse energies are also possible based on the power of the laser and the exposure area.

Figure 3B:
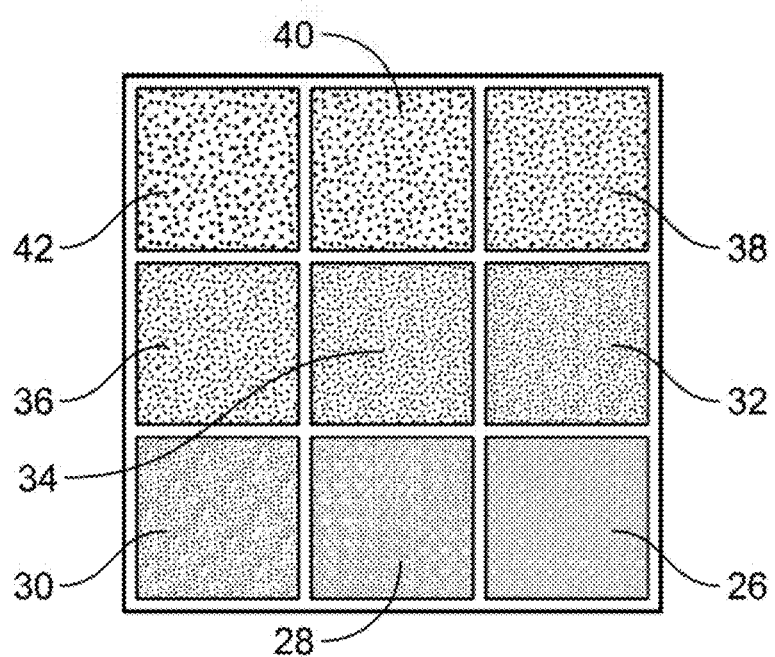
FIG. 3B is an end view of the matrix of FIG. 3A.

In an embodiment in FIGS. 3A and 3B, the sensitivity matrix 24 is comprised of a plurality of regions 26, 28, 30, 32, 34, 36, 38, 40, 42 that are each designated to allow a prescribed intensity of light to pass therethrough to assess an individual's minimum blistering dose tolerance and in turn optimally treat a patient at their maximum tolerable dose.

The sensitivity matrix 24 includes nine regions 26, 28, 30, 32, 34, 36, 38, 40, 42 that form a three by three matrix. However, the number of regions and arrangement can vary and the matrix 24 can be comprised of any number of regions that can be arranged in any desired matrix or pattern to change what would have otherwise been a single unique dose level into an array of multiple dose levels simultaneously covering the entire range of potentially applicable therapeutic treatment levels.

In an embodiment, the regions 26, 28, 30, 32, 34, 36, 38, 40, 42 of the sensitivity matrix 24 are comprised of absorptive and/or reflective material that allows for varying intensities of light to pass therethrough. In another embodiment, the regions 26, 28, 30, 32, 34, 36, 38, 40, 42 of the sensitivity matrix 24 are each comprised of partially transmissive material or filters that allows for varying intensities of light to pass therethrough. In an embodiment, the matrix 24 is comprised of fused silica optical components. In an embodiment, the regions 26, 28, 30, 32, 34, 36, 38, 40, 42 of the matrix 24 can be comprised of totally and/or partially reflective materials. The reflective materials can be a dielectric interference filter (e.g., partial reflector). In an embodiment, the filter can be a multi-dielectric interference filter. In an embodiment, the filter can be a metallic coating, including a dielectric enhanced metallic reflector. In an embodiment, the filter can be metallic and comprised of materials such as aluminum or silver. In an embodiment, the filter can be a combination of dielelectric interference filter, a multi-dielectric interference filter and a metallic coating.

In an embodiment, the filters reflect a fraction of a dose of energy between about 0% and 99% and segment the dose into multiple beams or streams of energy of varying intensities and transmit the multiple beams or streams of energy of varying intensities onto an individual.

Exposing a psoriatic area to high doses of UV light will cause faster clearing and place the skin condition into remission much faster and for a longer period of time than a lower dosage of UV light. As such, by directly testing diseased skin tissue to assess the optimal dose of laser treatment of psoriasis based on MBD allows for treatment to be close to the most aggressive and, therefore, more efficacious, but still well-tolerable dosage.

By treating a patient at or near their MBD, the number of treatment sessions required to place the diseased tissue into remission can be greatly reduced, and in an embodiment, such reduction in the number of treatments may achieve the desired result and yet decrease the total quantity or cumulative deposition of UVB light to which skin is exposed.

In an embodiment, the intensity of light that is able to pass through the regions 26, 28, 30, 32, 34, 36, 38, 40, 42 of the matrix 24 shown in FIGS. 3A and 3B can range from approximately about 20% to 100%. In another embodiment, intensity of light that is able to pass through the regions 26, 28, 30, 32, 34, 36, 38, 40, 42 of the matrix 24 can range from approximately about 20% to 90%. However, the number, shape and intensity of light being permissible to pass through the region 26, 28, 30, 32, 34, 36, 38, 40, 42 of the matrix 24 can vary and be greater or small than the numbers described herein.

Figure 4:
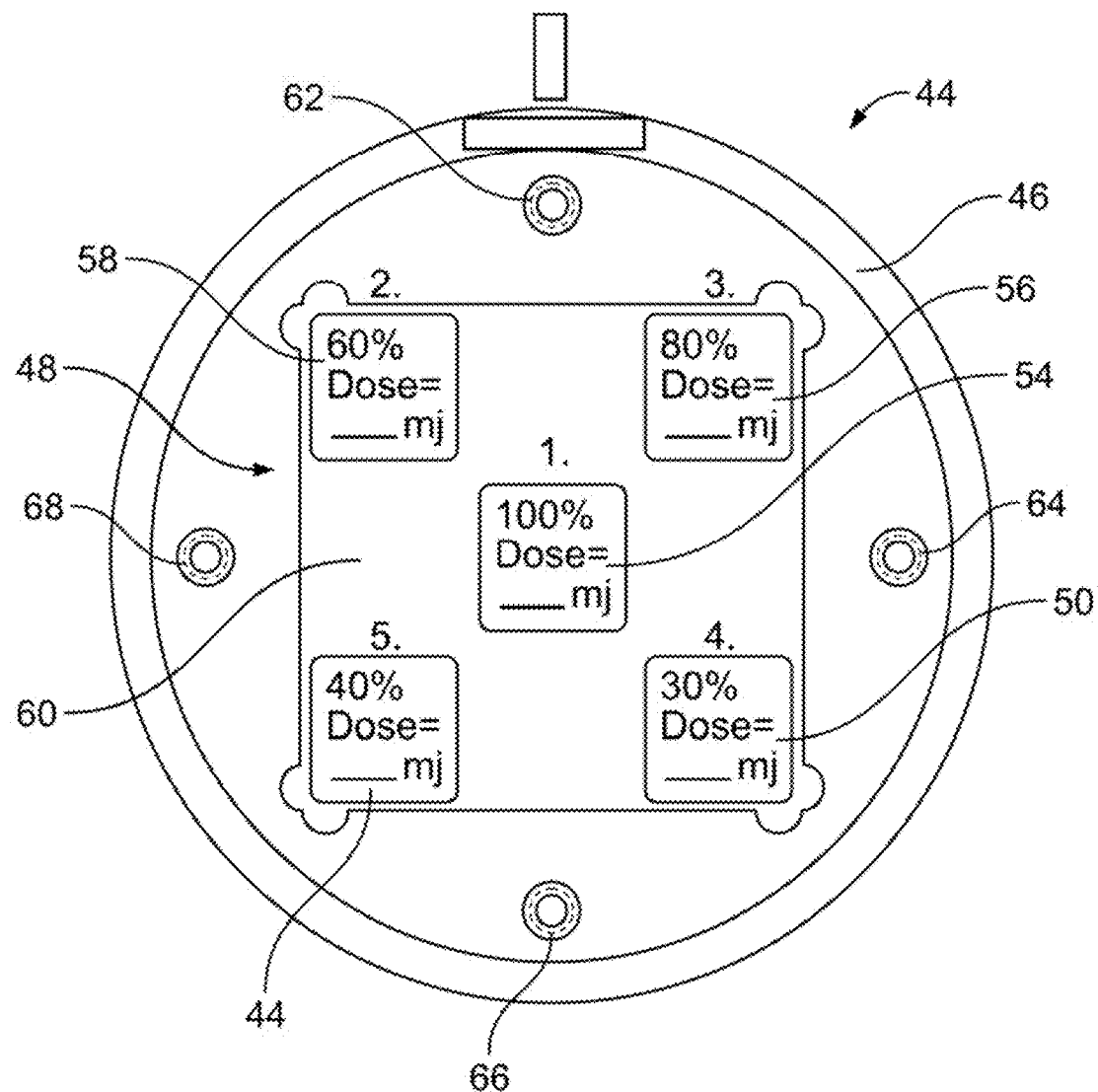
FIG. 4 is an end view of an embodiment of a dosimetry device of the present invention illustrating an embodiment of a photosensitivity matrix.
Figure 5:
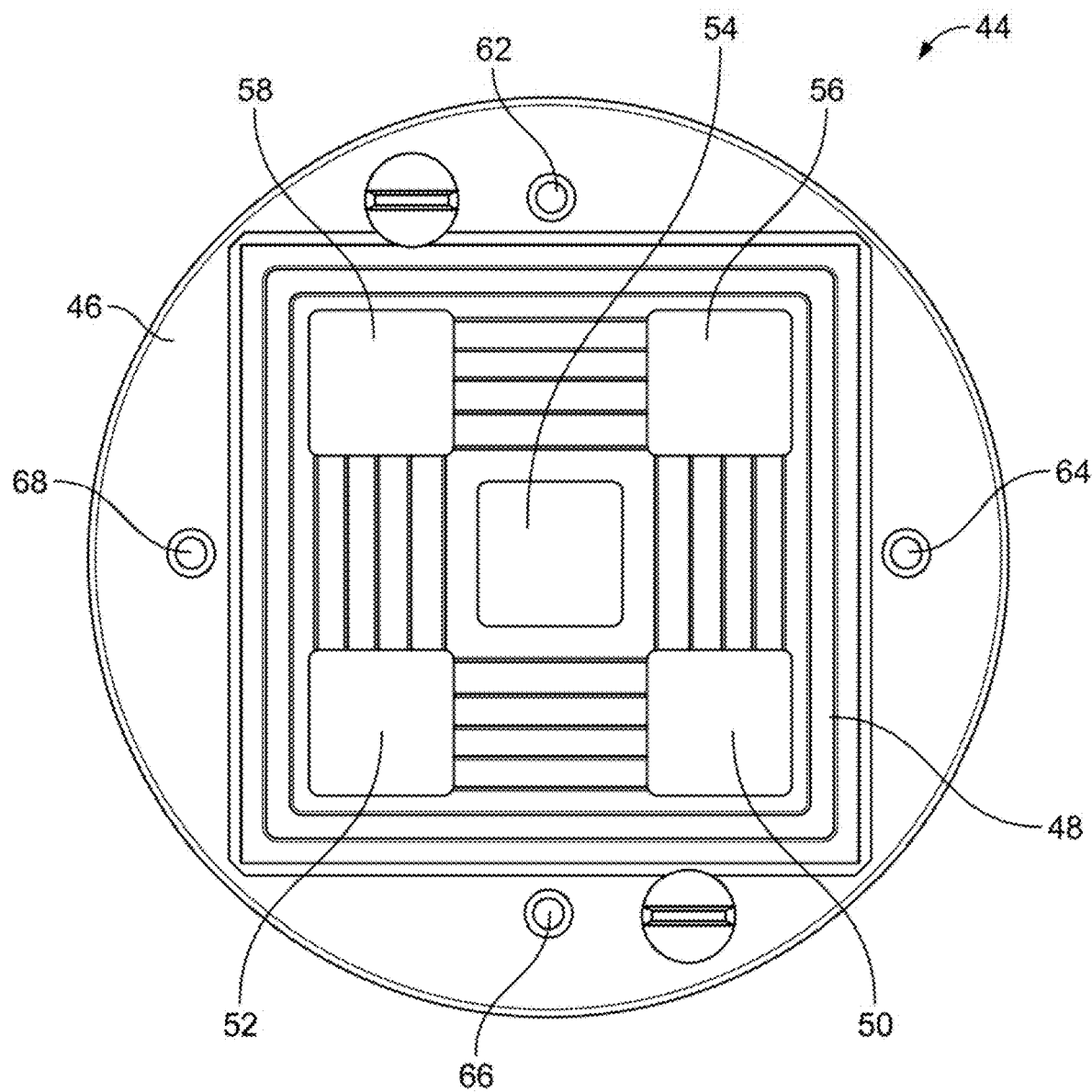
FIG. 5 is an end view of another embodiment of a dosimetry device of the present invention illustrating an embodiment of a photosensitivity matrix.

FIGS. 4 and 5 illustrate another embodiment of a dosimetry device 44. As shown, the dosimetry device 44 includes a housing 46 and a sensitivity matrix 48 that is comprised of a plurality of openings 50, 52, 54, 56, 58 formed therein. The matrix 48 is encapsulated by a UVB transparent optical window 60. In an embodiment, the matrix 48 can be a filter comprised of a single piece of glass, a plurality of different types of glass or crystalline materials. This filter can absorb varying percentages of a single incident dose of light, segment the energy into multiple beams or streams of energy of varying intensities and allow the various percentages of light to pass through and contact an individual's skin. To fix the device 52 to the laser delivery apparatus 10, in an embodiment, the device 44 includes a plurality of openings 62, 64, 66, 68 through which fasteners (not shown) can extend.

In an embodiment, the intensity of light that is able to pass through the openings 50, 52, 54, 56, 58 of the matrix 48 can range from approximately about 20% to 100%. In another embodiment, intensity of light that is able to pass through the openings 50, 52, 54, 56, 58 of the matrix 48 ranges from 20% to 90%. However, the number of openings, shape of the openings and intensity of light being permissible to pass through the openings of the matrix 48 can vary such that the number of openings can be greater or small than the numbers described herein.

In an embodiment, a single phototherapeutic dose of energy can be segmented directly into a plurality of beams of energy of different dosage levels using a filter arranged in a dosimetry device 12, 44. In another embodiment, two or more doses of energy are applied to an individual's skin through segmented filters arranged in a dosimetry device 12, 44 (e.g., a first dose test in a range of 100 to 500 mJ/cm2 and a second dose test in a range of 600 to 1000 mJ/cm2).

The device 12, 44 can be arranged in contact with an individual's body, the device 20, 44 can be releasably attached to an individual's body or the device 20, 44 can be arranged near an individual's body. The device 12, 44 can be reusable, disposable, and/or the sensitivity matrix 22, 54 can be replaced with a new or different matrix for each use or after a determined number of uses.

Figure 6:
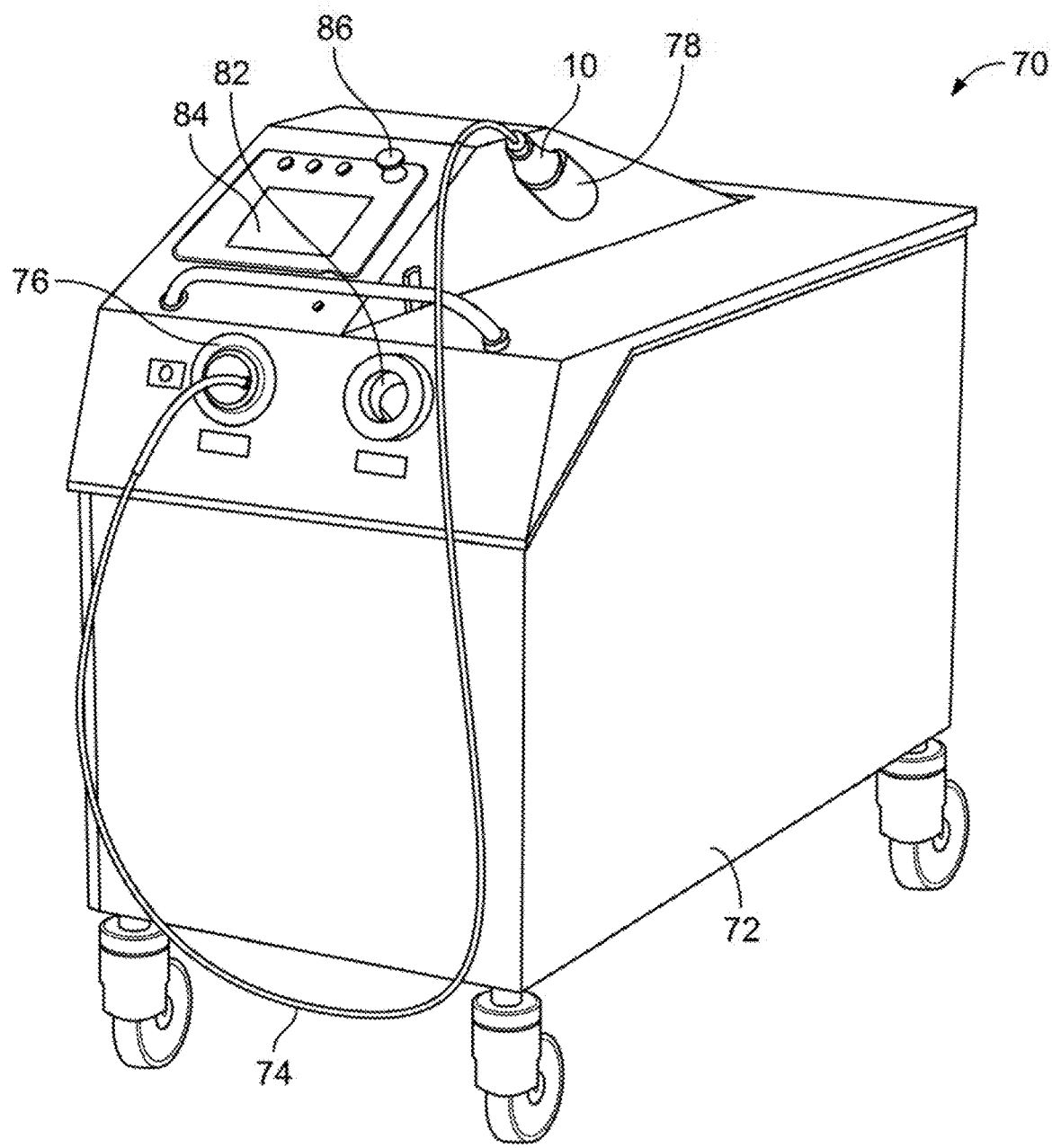
FIG. 6 is an embodiment of an excimer phototherapy system that is configured to delivery light energy through the photosensitivity matrix of a dosimetry device of the present invention.

FIG. 6 illustrates an embodiment of an excimer phototherapy system 70. The excimer phototherapy system 70 is designed to provide phototherapy for various dermatoses including psoriasis, vitiligo, leukoderma, atopic dermatitis, and alopecia by producing ultraviolet light energy within the UVB range (290-320 nm) of the electro-magnetic spectrum. Specifically, in an embodiment, the phototherapy system 70 is designed for treatment of various dermatoses in a narrow band, monochromatic wavelength at 308 nm for targeted phototherapy treatment, sparing healthy tissue from long-term cumulative UVB exposure. However, the delivery apparatus can distribute any form of energy in place of laser energy that is capable of treating various dermatoses.

The system 70 can be housed within and extend from a cart 72. The cart 72 includes a fiber-optic delivery cable 74 that is connected to the cart 72 at one end at a delivery port 76. The delivery apparatus, or hand piece, 10, which can rest in a hand piece cradle 78, is connected at the other end of the delivery cable 74. The hand piece 10, can include a user interface 80, which may be in the form of a pushbutton (See e.g., FIG. 1A) to control the delivery of energy (e.g., in the form of UVB light) from the system 70.

In order to perform a treatment session on an individual suffering from a skin condition, the hand piece 10 must first be calibrated. This can be done by placing the hand piece 10 in a calibration port 82 that extends into the cart 7. The cart 72 further includes, among other features, a control panel touch screen 84 for operation of the system 70 and an emergency stop switch 86.

To treat the diseased skin, after assessing a patient's tolerance, in an embodiment, ultraviolet light is delivered to each affected region of the body, for example, by an excimer laser, as described in U.S. Pat. Nos. 7,144,248 and 7,276,059, each herein incorporated by reference in their entirety. UV lamps, intense pulsed light ("IPL") devices, light-emitting diode ("LED") devices (e.g., available from Photo Therapeutics, Ltd. of Altrincham, United Kingdom and Photo Therapeutics, Inc. of Carlsbad, CA), or other phototherapy devices that are known or will be developed in the future can be employed to generate the UV light.

In an embodiment, ultraviolet light is directed only onto the affected regions. In an embodiment, ultraviolet light is directed onto the lesional as well as surrounding paralesional tissue, which although appearing normal is diseased tissue.

In an embodiment, phototherapy treatment of diseased psoriatic plaque can be combined with the use of a topical spray and/or ointment, such as clobetasol spray and calcitriol ointment to minimize phototoxicity. The use of a topical spray and/or ointment is typically used for the treatment of moderate-to-severe generalized psoriasis.

In some embodiments, phototherapy is administered or received without any help from a light-sensitizing agent. Alternatively, in an embodiment, light-sensitizing agents may be used, for example to increase the sensitivity of a cell to UV. In certain such embodiments, one or more light-sensitizing agents may be applied to the subject or received by the subject before or after phototherapy. Examples of light-sensitizing agents include, but are not limited to, coal tar, psoralen, acitretin, and salicylic acid. By avoiding treatment of unaffected portions of skin, the dosage can be raised well above conventional dosages as the affected areas will tolerate substantially higher doses without increased risk of side effects.

Figure 7:
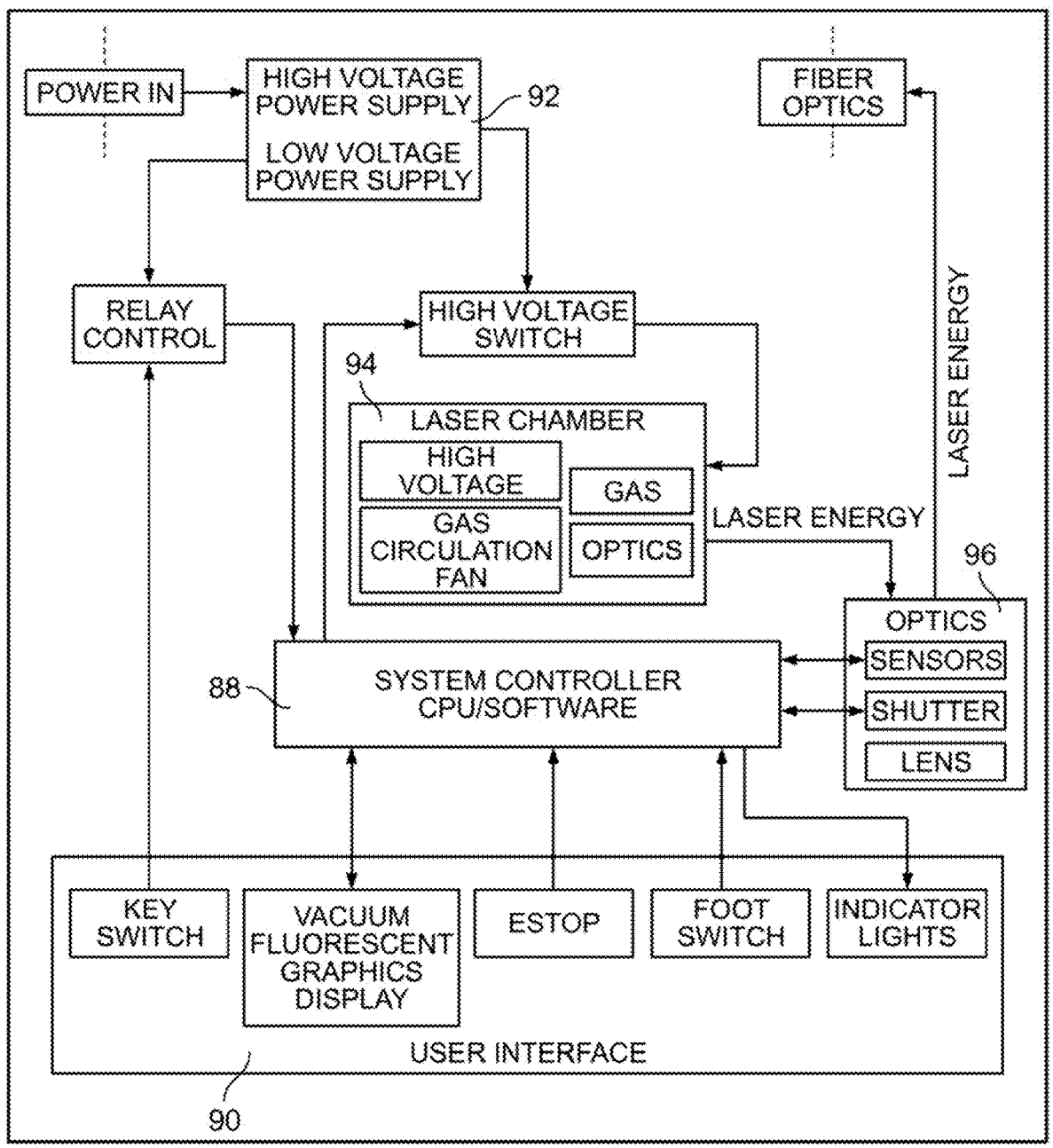
FIG. 7 is a schematic diagram depicting an embodiment of an excimer phototherapy system.
Figure 8:
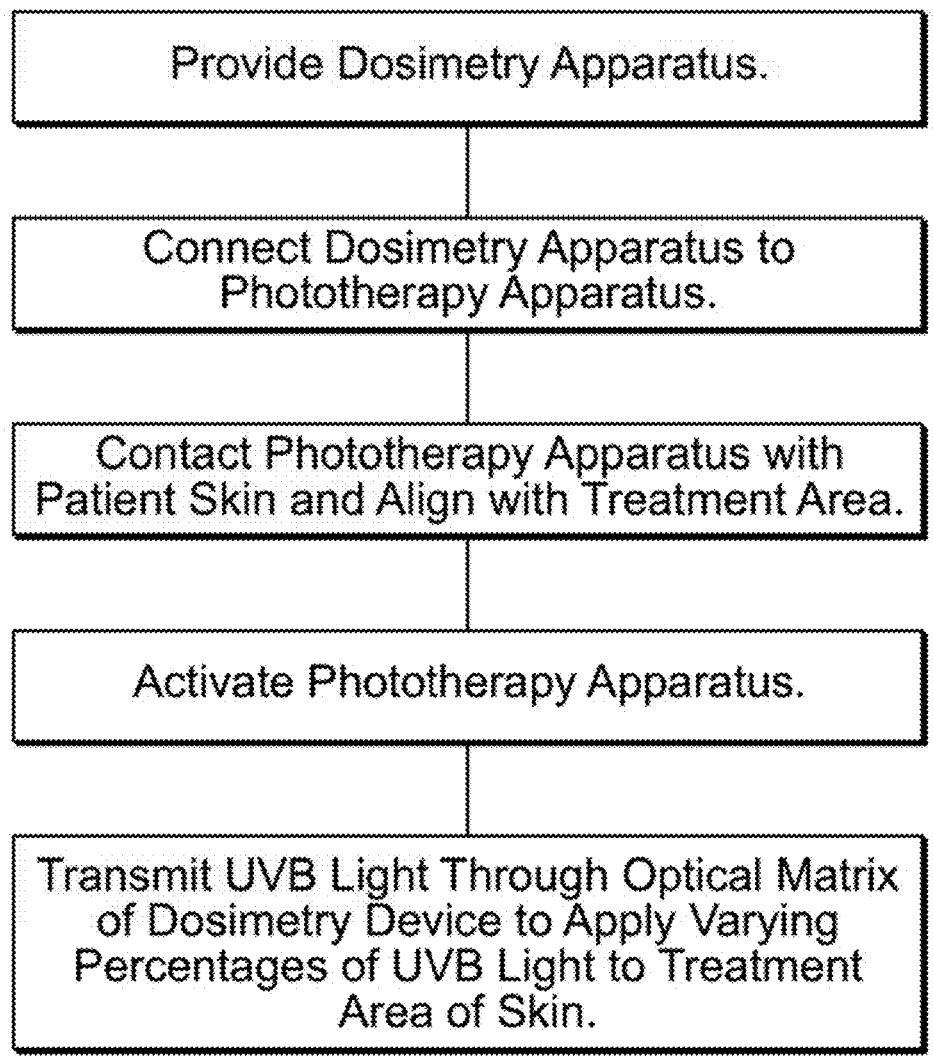
FIG. 8 is a flow chart outlining an embodiment of steps that can be taken to analyze a maximum tolerable dose of phototherapy that can be applied to a treatment area.

As shown schematically in an embodiment in FIG. 7, internal components of the excimer phototherapy system 70 can include a system controller (i.e., CPU/software) 88 that is capable of directly and/or indirectly interacting with a user interface 90, a power supply 92, a laser chamber 94 and optics components 96. Laser energy can be delivered from the system 70 by fiber optics to the hand piece 10 and onto an individual suffering from a skin condition.

In operation, upon determining a patient's MTD based on the results using the dosimetry device 12, 44, the total delivered dose, can be adjusted to optimize the effectiveness of the UVB dosing and minimize the number of required treatments and to ensure patient safety.

FIG. 7 illustrates a flow chart outlining an embodiment of steps that can be taken to analyze the MTD of phototherapy that can be applied to an individual suffering from a skin condition. As depicted in the flow chart, a dosimetry device can be provided that is then connected to the phototherapy apparatus. The phototherapy apparatus can then be placed near or in contact with a diseased region of an individual suffering from a skin condition. Once the device 12, 44 is orientated over a diseased region of skin, the delivery system 10 can then output a dose of UVB light that will travel through the matrix 20, 48 at varying intensities and contact a diseased region of skin at such varying intensities. Then, approximately 24 to 48 hours after applying the UVB dose of phototherapy to the diseased region of skin at varying intensities, the individual can then return to a clinician's office where the clinician can assess the tested area and determine the individual's MBD by observing which percentage(s) of the UVB light manifested a blistering response. By knowing the individual's MBD, the individual can subsequently be treated just below their MBD, at their optimal or MTD.

In an embodiment, an excimer laser can be used to generate short high power pulses of light having a wavelength of about 308 nanometers. These pulses can be high in peak power, e.g., about half a million watts, but short in duration, for example, lasting much less than about 100 nanoseconds (e.g., about 30 nanoseconds). The laser, however, may produce a plurality of such pulses at a repetition rate of about 100, 150, 200, 250, 300, 400, 450, or 500 Hz, and ranges therebetween. Tissue exposed to a plurality of these short pulses will increase in temperature slightly with application of each pulse. The cumulative effect of the plurality of pulses to raise the temperature of the tissue to a certain amount depends in part on the heat capacity of the tissue. The energy from the laser may be spread over a long enough period of time so as to permit sufficient dissipation to avoid excessive build-up of heat from the plurality of short pulses. Thermal damage caused by raising the temperature of the skin above, for example, the blister temperature of 50° C., can thereby be reduced, mitigated, or prevented. The duration of exposure of the affected tissue to the therapeutic doses of UV light, however, depends on the particular dose level.

FIG. 9 depicts the result of an exposure of a patient's skin to five different intensity levels resulting from application of the laser UV light through the endpiece depicted in FIG. 5. The limitation to only five different intensities is merely one possible embodiment. Five windows in the endpiece is not a critical number. The purpose of such exposure is to determine the optimum starting laser dose for a psoriasis lesion. For a single laser dose application, the tip simultaneously creates an array of typically five varying dose levels: 100%, 80%, 60%, 40% and 30%, where 100% is equivalent to the user-selected dose level. The array consists of five, 32 mm² separate squares spread symmetrically across the 4 cm² full laser aperture. Based on the skin reaction to the five different energy levels after 24-48 hours, the optimal starting dose can be determined. In practice, the user only has to count the number of blisters formed, as depicted in FIG. 9, to determine the minimal blistering dose (MBD).

FIG. 10A depicts a filter 100 that includes a plurality of windows that allow for various transmission levels of light to pass therethrough. The filter 100 can be fabricated from any 308 nm transmitting substrate such as fused silica or UV transmitting plastic such as acrylic or cyclic olefin copolymer. The substrates can be coated with any type of material that can achieve the desired transmission at 308 nm such as multi-layer dielectric materials or enhanced aluminum. As shown in FIG. 10B, the filter 100 can be included a tip assembly 102.

As an alternative, as shown in FIG. 10C, a filter 104, may be made from a thin metal membrane that is filled with a symmetric array of perforations. As shown in FIG. 10C, the filter 104 includes five perforations. The perforations can be chemically etched onto a single stainless steel membrane. FIG. 10D depicts exploded view of the tip assembly 106 that includes the filter 104.

Figure 11C:
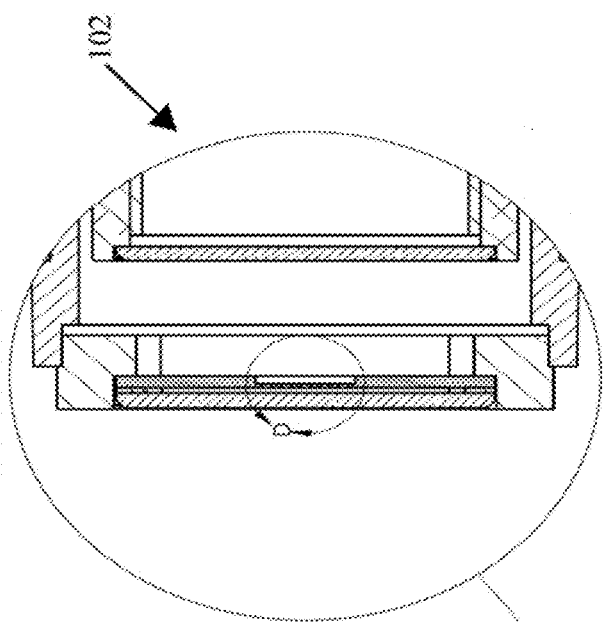
FIG. 11C is a detail view showing distribution of energy through a perforated panel of the tip assembly of FIG. 11A.
Figure 11A:
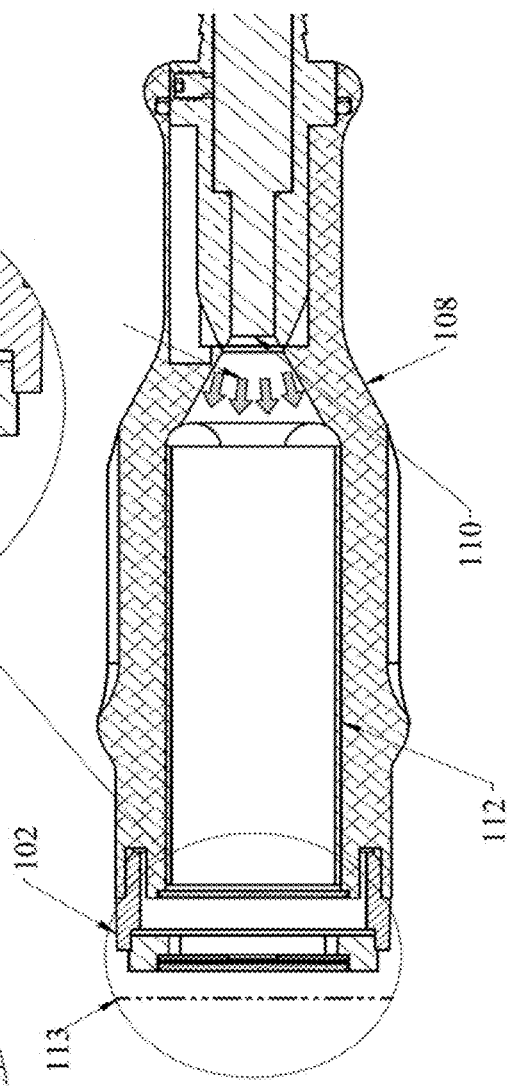
FIG. 11A is a cross-sectional view of a tip assembly that is attachable to a hand piece of an excimer phototherapy system.
Figure 11B:
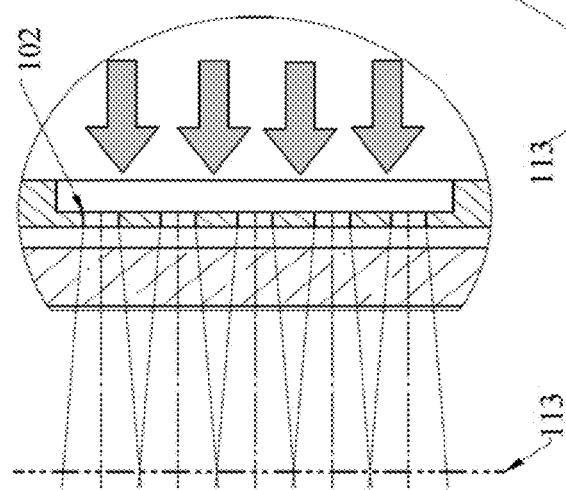
FIG. 11B is a detail view of the tip assembly of FIG. 11A.

FIG. 11A shows the tip assembly 102 attached to the delivery system, which can include a hand piece 108. In use, laser light that emerges from the fiber optic aperture 110 in the hand piece 108, is reflected by sidewall mirrors 112 and then passes into the tip assembly 102. The light is attenuated based on the transmission of the filters, passes through a protective A/R coated window 100 and illuminates the lesions on the skin at the plane 113 of uniform energy density (see FIGS. 11B and 11C). The optical design of the hand piece 108 defines the plane 113 of uniformity for the partially transmitting windows. This is a few millimeters from the exit plane of the tip assembly 102. For the perforated membrane 104, the plane of uniformity will also be influenced by the geometry of the perforations. Generally, coherent laser light impinging on an array of holes will generate an image of the holes in the near field and diffraction pattern in the far field. At reasonable distances from the hand piece aperture, these patterns are quite non-uniform and would not be suitable for uniform illumination. However, the laser light emerging from the optical fiber can be considered a quasi-extended light source. This is due to the fact that the radiation mixes during its progression through the light guide via many internal reflections. The light emerging into the hand piece will have many exit angles, which will be spread across the 3 mm fiber output aperture. Upon transmission through each perforation a "penumbra" will be generated (typical of extended light sources) which allows the light to fill in laterally and can result in an increase in lateral uniformity at a reasonable distance from the perforations. The uniformity of the light can be increased such that it will be within the specification of the window transmission tolerance (±2%) at the plane of uniform energy density.

Figure 12:
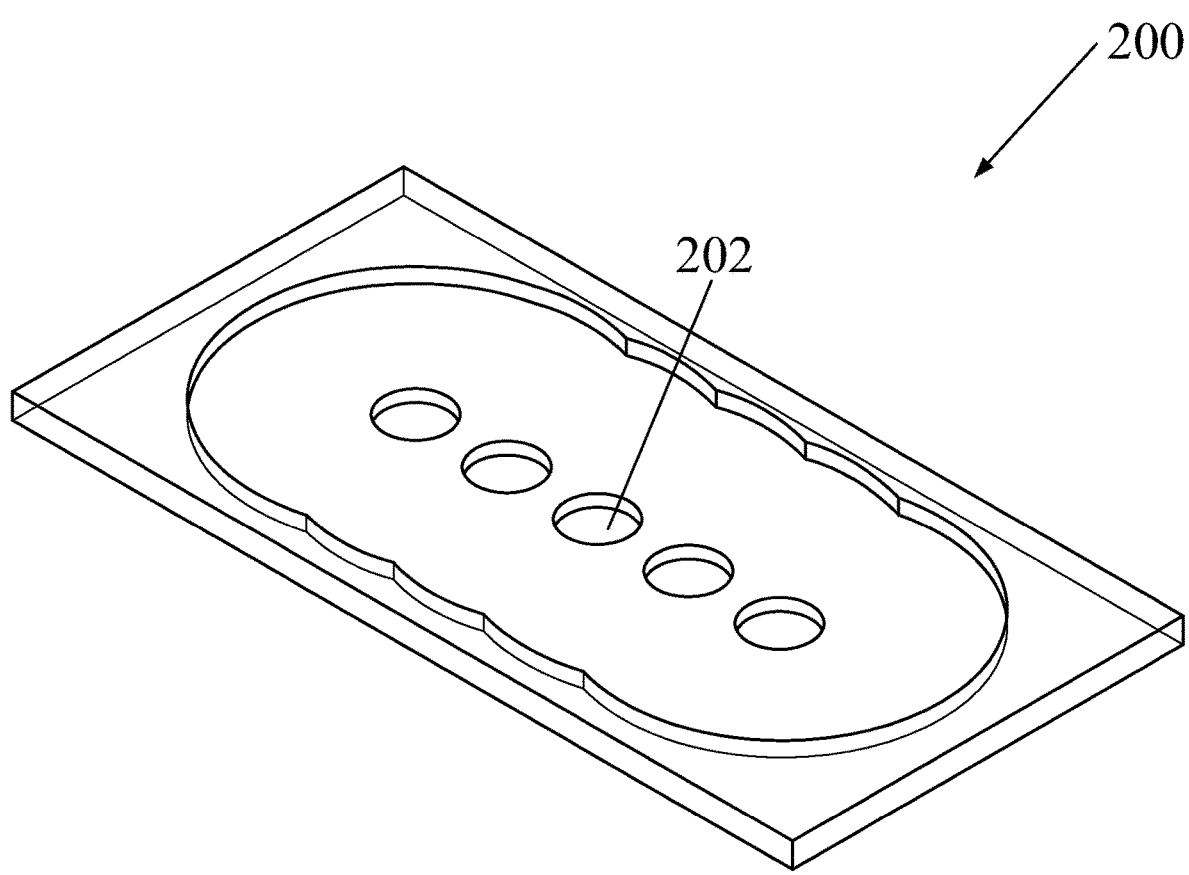
FIG. 12 is a perspective view of an embodiment of a tip assembly that can be associated with an excimer phototherapy system.

Alternatively, as shown in an embodiment in FIG. 12, a cap 200 can include an array of openings 202 that are used for determining the maximum blister dose a patient can sustain by using the top 200 in conjunction with a laser to accurately output different intensities through each openings 202. The cap 200 can be placed over the tip of the hand piece and using a notched shield 204, would group the exposed test area to about 1.5" and still give the necessary blister bracketing. The pattern could also be circular instead of linear.

Figure 13:
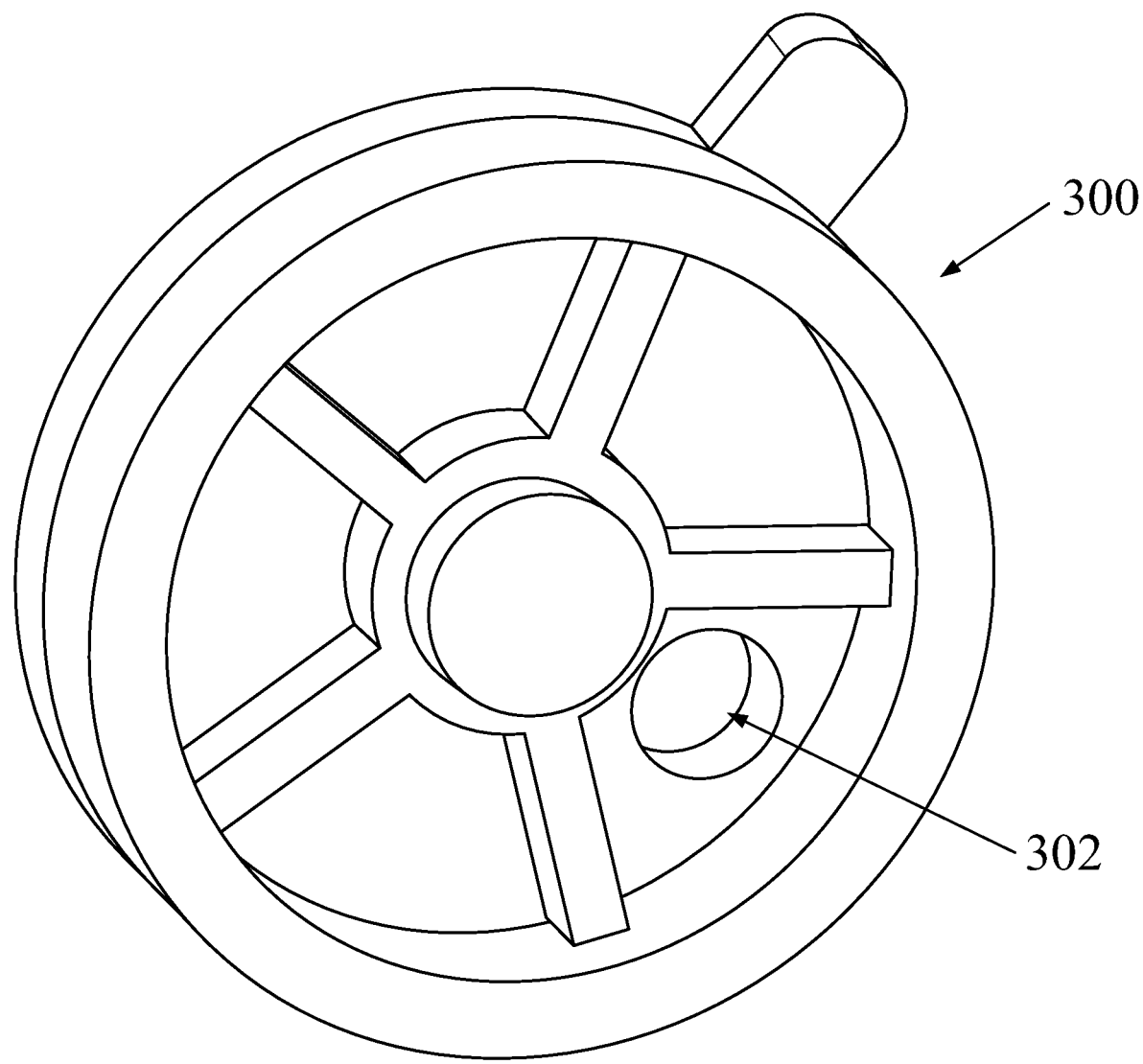
FIG. 13 is a perspective view of a cap that can be placed over an end piece of an excimer phototherapy system.

FIG. 13 illustrates an embodiment of a cap 300, which includes a single hole 302, and can rotate through a plurality of positions to lead the user through dosing different doses after each of which the aperture is rotated proportionately depending on the number of positions of a full rotation (e.g., as shown there are five positions so each rotation is ⅕ a full rotation of the cap 300). The cap 300 can be spring-loaded, with a ratchet indexer to facilitate the aperture rotation. The method for determining the proper dose would again be by counting the blisters (e.g., if the. user selects a 1000 mJ dosage, the skin of a patient can be exposed to 1000 mJ, 800 mJ, 600 mJ, 400 mJ and 200 mJ to assess reactivity of the patient's skin to different dosage levels).

While reference has been made to specific embodiments described using specific terms, such description is for illustrative purposes only, and it is to be understood that modifications and variations to such embodiment, including, but not limited to, the substitution of equivalent features, materials, or parts, and the reversal of various features thereof, may be practiced by those of ordinary skill in the art without departing from the spirit and scope of the invention. As such, the drawings and the description are not to be taken as restrictive of the scope and are understood as broad and general teachings in accordance with the present invention.

What is claimed is:

1. A dosimetry device that is connectable to a phototherapy apparatus to apply a targeted dose of UVB light to a treatment area of diseased tissue to determine a minimal blistering dose, the dosimetry device comprising:

a tubular housing having a sidewall with an outer surface and an inner surface extending along an axis between a first end and a second end, which is spaced from the first end, the housing defining a single cavity extending contiguously along the axis about the inner surface of the sidewall between a single opening at the first end and a single opening at a second end, the cavity being devoid of a light source arranged therein, and the first end of the sidewall configured to be releasably connected directly to a distal end of a hand piece of the phototherapy apparatus that is configured to distribute the targeted dose of the UVB light through the housing to the treatment area of the diseased tissue to determine the minimal blistering dose; and a single optical matrix including a plurality of transmissive regions that include at least a first transmissive region and a second transmissive region that are at least one of connected to and formed within the housing at the second end of the sidewall of the housing, wherein at least one of the transmissive regions includes at least one of a metallic, multi-dielectric and a dielectric coating that is configured to reduce an intensity of the UVB light passing through the housing and the at least one of the transmissive regions, and wherein each of the plurality of light transmissive regions each permits a different transmission of the UVB light to pass therethrough and contact the treatment area of the diseased skin.

2. The dosimetry device of claim 1, wherein the plurality of transmissive regions comprises fused silica.

3. The dosimetry device of claim 1, wherein the plurality of transmissive regions comprises UV transmitting plastic.

4. The dosimetry device of claim 3, wherein the transmitting plastic is acrylic or cyclic olefin copolymer.

5. The dosimetry device of claim 4, wherein the transmitting plastic is coated with multi-layer dielectric materials.

6. The dosimetry device of claim 5, wherein the transmitting plastic is coated with enhanced aluminum.

7. The dosimetry device of claim 1, wherein the transmission of the UVB light passing through the transmissive regions ranges from about 20% in one region up to about 100% in another region.

8. The dosimetry device of claim 1, wherein the transmission of the UVB light passing through the transmissive regions ranges from about 0% in one region up to about 90% in another region.

9. The dosimetry device of claim 1, wherein the optical matrix is substantially square.

10. The dosimetry device of claim 1, wherein each of the plurality of transmissive regions of the optical matrix are square, rectangular, circular or ovoid.

11. The dosimetry device of claim 1, wherein each of the transmissive regions include at least one of a metallic, multi-dielectric and a dielectric coating or volume absorbing materials in a UVB range.

12. The dosimetry device of claim 1, wherein the hand piece is configured to transmit the UVB light to the dosimetry device.

13. The dosimetry device of claim 12, wherein the housing of the dosimetry device further includes at least one tab, the at least one tab being configured to releasably connect the housing of the dosimetry device to the hand piece.

14. A method of determining a maximum tolerable dose of phototherapy that is capable of being applied to a treatment area, the method comprising the following steps:

providing a tubular housing having a sidewall with an outer surface and an inner surface extending along an axis between a first end and a second end, which is spaced from the first end, the housing defining a single cavity extending contiguously along the axis about the inner surface of the sidewall between a single opening at the first end and a single opening at a second end, the cavity being devoid of a light source arranged therein, and the first end of the sidewall configured to be releasably connected directly to a distal end of a hand piece of the phototherapy apparatus that is configured to distribute the targeted dose of the UVB light through the housing to the treatment area of the diseased tissue to determine a minimal blistering dose; and a single optical matrix including a plurality of transmissive regions that include at least a first transmissive region and a second transmissive region that are at least one of connected to and formed within the housing at the second end of the sidewall of the housing, wherein at least one of the transmissive regions includes at least one of a metallic, multi-dielectric and a dielectric coating that is configured to reduce an intensity of the UVB light passing through the housing and the at least one of the transmissive regions, and wherein each of the plurality of light transmissive regions each permits a different transmission of the UVB light to pass therethrough and contact the treatment area of the diseased skin;

connecting the housing to a phototherapy apparatus that is configured to dispense UVB light to the treatment area;

arranging the housing near the treatment area; and transmitting the UVB light from the phototherapy apparatus through the cavity in the housing.

15. The method of claim 14, wherein the housing includes a jig and a plurality of openings formed therein and the method comprising moving the jig about the diseased tissue to expose the diseased tissue to varying radiation levels applied through the openings to assess an optimal dosage.

16. The method of claim 15, wherein the percentages of the UVB light passing through positions of the jig ranges from about 20% in one region up to about 100% in another region.

17. The method of claim 15, wherein the percentages of the UVB light passing through the positions of the jig ranges from about 0% in one region up to about 90% in another region.

18. The method of claim 14, wherein the phototherapy apparatus transmits the UVB light at approximately about 308 nm.

19. The method of claim 14, further comprising the step of analyzing the treatment area subsequent to transmitting the varying percentages of the UVB light to the treatment area through the optical matrix to assess the minimum blistering dose of the treatment area.

20. The method of claim 14, wherein the treatment area is analyzed approximately 24 to 48 hours after the varying percentages of the UVB light are applied thereto to assess the minimum blistering dose of skin being treated by counting a number of blistered regions.

21. The method of claim 15, further comprising the step of applying the maximum tolerable dose of the UVB light to the treatment area based on a determination of the minimum blistering dose of the UVB light from an analysis of the varying percentages of the UVB light to the treatment area through the optical matrix or the jig to determine a near optimum therapeutic dose without blistering of the treatment area.

* * * * *